United States Patent [19]

Zakula

[11] Patent Number: 5,092,770
[45] Date of Patent: Mar. 3, 1992

[54] DENTURE ANCHORING SYSTEM

[76] Inventor: Michael R. Zakula, SR1, Box 5B, Ely, Nev. 89301

[21] Appl. No.: 475,226

[22] Filed: Feb. 5, 1990

[51] Int. Cl.⁵ .......................... A61C 13/12; A61C 5/08
[52] U.S. Cl. ..................................... 433/172; 433/219
[58] Field of Search ............... 433/172, 173, 219, 220, 433/174, 175, 176

[56] References Cited

U.S. PATENT DOCUMENTS

| | | | |
|---|---|---|---|
| 711,324 | 10/1902 | Lacy | 433/173 |
| 3,656,236 | 4/1972 | Kurer | 433/174 X |
| 4,488,875 | 12/1984 | Niznick | 433/173 |
| 4,547,156 | 10/1985 | Hader | 433/172 |
| 4,568,285 | 2/1986 | Chiaramonte et al. | 433/173 |
| 4,682,951 | 7/1987 | Linkow | 433/173 |
| 4,881,897 | 11/1989 | Franek et al. | 433/173 X |

FOREIGN PATENT DOCUMENTS

| | | | |
|---|---|---|---|
| 2502036 | 7/1976 | Fed. Rep. of Germany | 433/173 |
| 3525298 | 1/1987 | Fed. Rep. of Germany | 433/172 |
| 3812952 | 11/1989 | Fed. Rep. of Germany | 433/172 |
| 548504 | 10/1922 | France | 433/174 |
| 594500 | 6/1959 | Italy | 433/220 |
| 8706121 | 10/1987 | World Int. Prop. O. | 433/172 |

Primary Examiner—Robert P. Swiatek
Assistant Examiner—Nicholas D. Lucchesi
Attorney, Agent, or Firm—Mallinckrodt & Mallinckrodt

[57] ABSTRACT

An improved system for anchoring a partial or full denture in place provides one of the anchor members of the usual pair of matingly interconnecting anchor members in two separate parts, rather than a single unitary part, so that the base part thereof can be embedded permanently in the tooth-holding material of the denture and the other part thereof, which is the matingly interconnecting part, is adapted to matingly interconnect with the other anchor member of the pair of such anchor members in the usual manner, the two separate parts being themselves matingly interconnected, as by screw threads, for quick and easy separation and engagement of a replacement matingly interconnecting part when necessary because of wear.

7 Claims, 1 Drawing Sheet

DENTURE ANCHORING SYSTEM

BACKGROUND OF THE INVENTION

1. Field:

The invention is in the field of dentistry and has to do with the anchoring of overdentures and partial dentures to tooth roots that remain after removal therefrom of the normally associated natural teeth.

2. State of the Art:

A variety of systems have been developed heretofore and are in more or less satisfactory use for removably retaining so-called "overdentures" and partial dentures in the mouth by anchoring them to one or more tooth roots remaining after removal of the teeth therefrom down to the vicinity of the gum line.

In several of these prior art systems, a female member of at least one pair of anchor members is placed in the natural tooth root and root canal as prepared to receive the same and is firmly secured therein, as by cementing. Such female member is usually made of stainless steel. Various types of male members are used depending upon the particular system.

In one of the prior art systems, the male member of a pair of anchor members is a post of nylon plastic having a ball-shaped head for snapping into the female member to provide resiliency, rotational freedom, and ease of placement of the denture in and removal from the mouth of the dental patient. The base of such male member is firmly embedded in the material of the denture, which is allowed to cure about such base of the male member. A centering sleeve is normally placed on the exposed shank of the male member during the embedding procedure as an aid to maintaining proper mating interengaging placement of the male and female pair of anchor members.

A problem associated with this otherwise very effective and convenient system is the fact that the ball-headed male member is subject to wear and must be replaced frequently. This involves excavation of the denture material, usually an acrylic plastic, surrounding the base of the male member, insertion of the base of a replacement male member in the excavation, and the placement of fresh denture material in the excavation surrounding the base of the new male member so as to firmly secure such new male member in place upon setting up of the newly placed denture material.

SUMMARY OF THE INVENTION

A principal objective in the making of the present invention was to eliminate the need for first excavating the base of the male member of the pair of anchor members from the denture and for then placing fresh denture material in the resulting excavation when replacing a worn male member, but still preserving the advantages of the particular system concerned and prolonging the life of the denture whether partial or full.

In the accomplishment of this objective, the unitary male member of the pair of anchor members is replaced, in accordance with the invention, by a two-part male member. The two separate parts are formed for mating interaction, so one of such parts can be permanently embedded in the denture as a base part and the other part can be removably interengaged therewith as the exposed mating member of the pair of anchor members of the system.

THE DRAWINGS

In the drawing, which illustrate the best mode presently contemplated for carrying out the invention in actual practice:

FIG. 1 represents a top plan view of an overdenture constituting the lower plate of a set of dentures for a dental patient;

FIG. 2, a vertical section, partially in elevation, taken along the line 2—2 of FIG. 1 and drawn to a larger scale, showing the lower plate of FIG. 1 anchored in place in the mouth of the dental patient, only the lower gums and a tooth root to which such plate is anchored being shown; and FIG. 3, an exploded view of the pair of anchor members of FIG. 2, the worn ball-headed part of the male anchor member having been removed from the embedded base part so that a new ball-headed part can be inserted in the embedded base part.

DETAILED DESCRIPTION OF THE ILLUSTRATED EMBODIMENT

Figure 1:
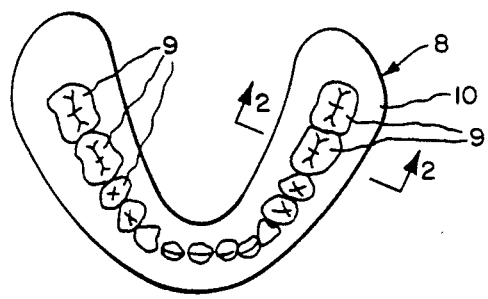

In the illustrated embodiment of the invention, an overdenture 8 made up in the usual way and comprising a set of teeth 9 anchored in a standard denture material 10, such as pink acrylic plastic, is shown in FIG. 1 as the lower plate of the usual pair of upper and lower dentures for a dental patient.

Figure 2:
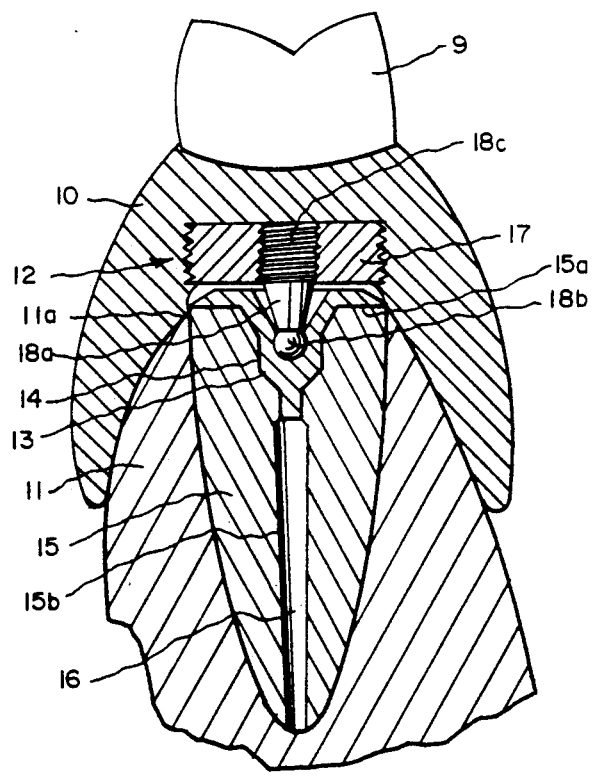

In FIG. 2, such lower plate of the pair of dentures is shown as being removably anchored in the mouth of the patient, resting against the lower, normally toothed, gum ridge 11 of the patient's mouth. The overdenture, i.e., denture plate, 8 is held in place by oppositely positioned anchor members 12 and 13 secured in the acrylic denture material 10 and in a tooth root at the gum ridge 11, respectively.

The anchor members 12 and 13 are matingly interengageable, one of which, here the anchor member 13, being of female formation and the other, the anchor member 12, being of male formation.

In this illustrated embodiment, anchor member 13 is of stainless steel and is permanently held within a reentrant recess 14 drilled in customary manner within the root 15 of a natural tooth which has been sliced off in customary manner along approximately the horizontal at 15a in the vicinity of the gumline 11a. Recess 14 is drilled inwardly of tooth root 15 from the relatively flat face 15a thereof to root canal 15b, so that the lower face of the annular portion 13a. Female anchor member 13 is flush with such face 15a, FIG. 2, of tooth root 15 when installed in the recess 14 prepared for receiving it. As is customary, female anchor member 13 is secured firmly in place by cementing it to the confronting faces of the receiving recess and to the usual filling material 16 placed in root canal 15b.

Whereas in the prior art the male member is molded from nylon plastic as a unitary piece, in accordance with the present invention the male member 12 is made in two parts. In the illustrated embodiment, one part 17 provides a base for embedding in the acrylic material 10 of the denture plate 8 essentially flush with where the natural tooth has been sliced off, and the other part 18 provides a post 18a with a ball-headed end 18b. Note that ball-headed end 18b is of no more length than is required to reach from the base part just above the top of the other anchor member to the interconnecting portion of the other anchor member that matingly interconnects with it. The base part 17 is preferably a stainless steel annulus internally threaded at 17a to receive the externally threaded opposite end 18c of part 18, which is preferably fabricated from nylon.

Figure 3:
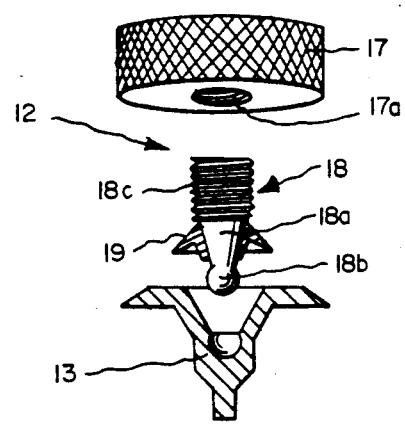

As is usual, a centering sleeve 19, FIG. 3, may be slipped over the ball-headed end 18b of post 18a to facilitate orientation of the anchor members 12 and 13 during the placement of same in the acrylic denture material 10 and in tooth root 15 of the dental patient, respectively. Such sleeve is removed after the acrylic material is set and plays no part in the actual anchoring of denture plate 8 in the mouth of the user.

The system of the invention enables a worn interengaging part, usually a male part, of a pair of interengaging anchor members to be quickly and easily replaced, without excavation and replacement of denture material as is necessary in prior art systems. As shown in the illustrated best mode presently contemplated, screw threaded interengagement of the one part of the two part anchor member to the other part thereof is presently preferred, as is the snap-in interengagement of male and female anchor members presently employed by certain of the prior art systems.

Whereas this invention is here illustrated and described with specific reference to an embodiment thereof presently contemplated as the best mode of carrying out such invention in actual practice, it is to be understood that various changes may be made in adapting the invention to different embodiments without departing from the broader inventive concepts disclosed herein and comprehended by the claims that follow.

I claim:

1. An improved denture anchoring system for a full or partial denture made up of a tooth or teeth secured in a tooth-holding denture material, comprising a pair of matingly interconnecting anchor members, one of which is subject to wear and requires frequent replacement, said one anchor member being made in two separate parts, one part of which is formed as a base with an opening, said base part being adapted for embedding in said tooth-holding denture material with its said opening exposed substantially flush with and exteriorly of said denture material, and the other part of which is formed for engagement with the other of said anchor members which is adapted for permanent securement in and substantially flush with the exposed surface of the root of a normal tooth which has been sliced off in the vicinity of the gum line of a dental patient, said other part being subject to wear, said one anchor member, except for said base part, remaining entirely free of said denture material, whereby said other part of said one anchor member that is subject to wear may be removed and replaced without disturbance of said denture material, said base part of the one part of the one anchor member being embedded in denture material holding a denture tooth in a person's mouth, the opening of said base part being exposed substantially flush with and exteriorly of said denture material, and said other of the anchor members being permanently secured in the root of a normal tooth of said person that has been sliced off in the vicinity of the gum line of said person, said other part of the said one part of the one anchor member being engaged with said other of the anchor members, whereby said denture tooth held by said denture material is securely anchored in said person's mouth.

2. An improved denture anchoring system according to claim 1, wherein the base part of the one anchor member subject to wear is an annulus that is internally threaded as a female part and the other part of the said one anchor member subject to wear has an anchor-member-interengaging end subject to wear and an opposite end that is externally threaded as a male part in screw interengagement with the internal threads of said female part.

3. An improved denture anchoring system according to claim 2, wherein the base part of the one anchor member subject to wear is an annulus of stainless steel and the anchor-member-interengaging end of the other part is molded to shape from a plastic material.

4. An improved denture anchoring system according to claim 3, wherein the plastic material is nylon.

5. An improved denture anchoring system according to claim 1, wherein the pair of matingly interconnecting anchor members are constructed and arranged to snap together into and out of interengagement.

6. In a method of anchoring a full or partial artificial denture made up of a tooth or teeth secured in a tooth-holding denture material and having for at least one tooth of said denture a pair of matingly interconnecting anchor members, one of which is subject to wear and requires frequent replacement and is embedded in said denture material and the other of which is permanently secured in the root of a normal tooth which has been sliced off in the vicinity of the gum line of a dental patient, the improvement comprising:

making the said one anchor member in two parts;
forming one part as a base with an opening;
embedding said base in said denture material with its opening exposed substantially flush with and exteriorly of said denture material;
forming the other part with a shank adapted for interengagement with said opening in the base; and
engaging said other part into the said opening of said base free and clear of said denture material so it can be removed and replaced without disturbing said denture material.

7. A method according to claim 6 wherein the opening in said base is internally threaded and said shank is externally threaded so as to interengage with said internally threaded opening of said base.

* * * * *